United States Patent
Tasar et al.

(10) Patent No.: US 11,893,820 B2
(45) Date of Patent: Feb. 6, 2024

(54) METHOD OF CREATING A PERSONAL BIOELECTRIC ID (PASSWORD) WITH HAND MOVEMENTS OF PERSON AND IDENTIFICATION OF BEHAVIORAL BIOMETRIC BASED PERSON WITH EMG SIGNALS

(71) Applicant: FIRAT UNIVERSITESI REKTORLUGU, Elazig (TR)

(72) Inventors: Beyda Tasar, Elazig (TR); Arif Gulten, Elazig (TR); Oguz Yakut, Elazig (TR)

(73) Assignee: FIRAT UNIVERSITESI REKTORLUGU, Elazig (TR)

( * ) Notice: Subject to any disclaimer, the term of this patent is extended or adjusted under 35 U.S.C. 154(b) by 373 days.

(21) Appl. No.: 17/286,831

(22) PCT Filed: Nov. 1, 2019

(86) PCT No.: PCT/TR2019/050916
§ 371 (c)(1),
(2) Date: Apr. 20, 2021

(87) PCT Pub. No.: WO2020/096553
PCT Pub. Date: May 14, 2020

(65) Prior Publication Data
US 2021/0334567 A1    Oct. 28, 2021

(30) Foreign Application Priority Data
Nov. 7, 2018    (TR) ................... 2018/16762

(51) Int. Cl.
*G06K 9/00*    (2022.01)
*G06F 3/01*    (2006.01)
(Continued)

(52) U.S. Cl.
CPC .............. *G06V 40/10* (2022.01); *A61B 5/389* (2021.01); *G06F 3/015* (2013.01); *G06F 21/32* (2013.01); *G06V 40/28* (2022.01); *G06V 40/15* (2022.01)

(58) Field of Classification Search
CPC .......... G06K 9/00885; G06K 9/00355; G06K 2009/00939; G06F 3/015; G06F 21/32
See application file for complete search history.

(56) References Cited

U.S. PATENT DOCUMENTS

| 10,943,100 B2 * | 3/2021 | Tadi | G06F 18/245 |
| 2014/0304792 A1 * | 10/2014 | Derchak | A61B 5/6824 726/7 |
| 2019/0034797 A1 * | 1/2019 | Sakai | G06N 3/08 |

FOREIGN PATENT DOCUMENTS

| JP | 2018041202 A * | 3/2018 | |
| WO | WO-2018002722 A1 * | 1/2018 | ......... A41D 13/1281 |

OTHER PUBLICATIONS

"Filter Design and Performance Evaluation for Fingerprint Image Segmentation"—Thai et al., PLOS One, May 12, 2016 https://journals.plos.org/plosone/article/file?id=10.1371/journal.pone.0154160&type=printable (Year: 2016).*
(Continued)

*Primary Examiner* — Randy A Scott
(74) *Attorney, Agent, or Firm* — Bayramoglu Law Offices LLC

(57) ABSTRACT

A method—for biometric based person recognition systems is provided. The method provides an identification of a personalized bioelectric code and a personal ID code by identifying persons and gestures of a person with a benefit of behavioral biometric data of Electromyography (EMG) signals. The method includes the steps of: making the person wishing to create a password to wear a wristband, simultaneously recording of hand movements in eight bioelectric (Continued)

signals from eight EMG sensors in recordings of up to 10 seconds, repeating each selected movement type by the person at least ten times, clearing a recorded raw signal group from noise signals with a bandpass filter, separating a signal cleaned from the noise signals into to windows, creating a customized behavioral biometric data set with generated attributes for each transaction, obtaining the personalized bioelectrical code and the personal ID code.

1 Claim, 1 Drawing Sheet

(51) Int. Cl.
*G06F 21/32* (2013.01)
*G06V 40/10* (2022.01)
*G06V 40/20* (2022.01)
*A61B 5/389* (2021.01)

(56) References Cited

OTHER PUBLICATIONS

"Biometric Identification Based on the Eye Movements and Graph Matching Techniques"—Rigas et al., Pattern Recognition Letters, vol. 33, Issue 6, Apr. 15, 2012 https://www.sciencedirect.com/science/article/pii/S0167865512000062 (Year: 2012).*

* cited by examiner

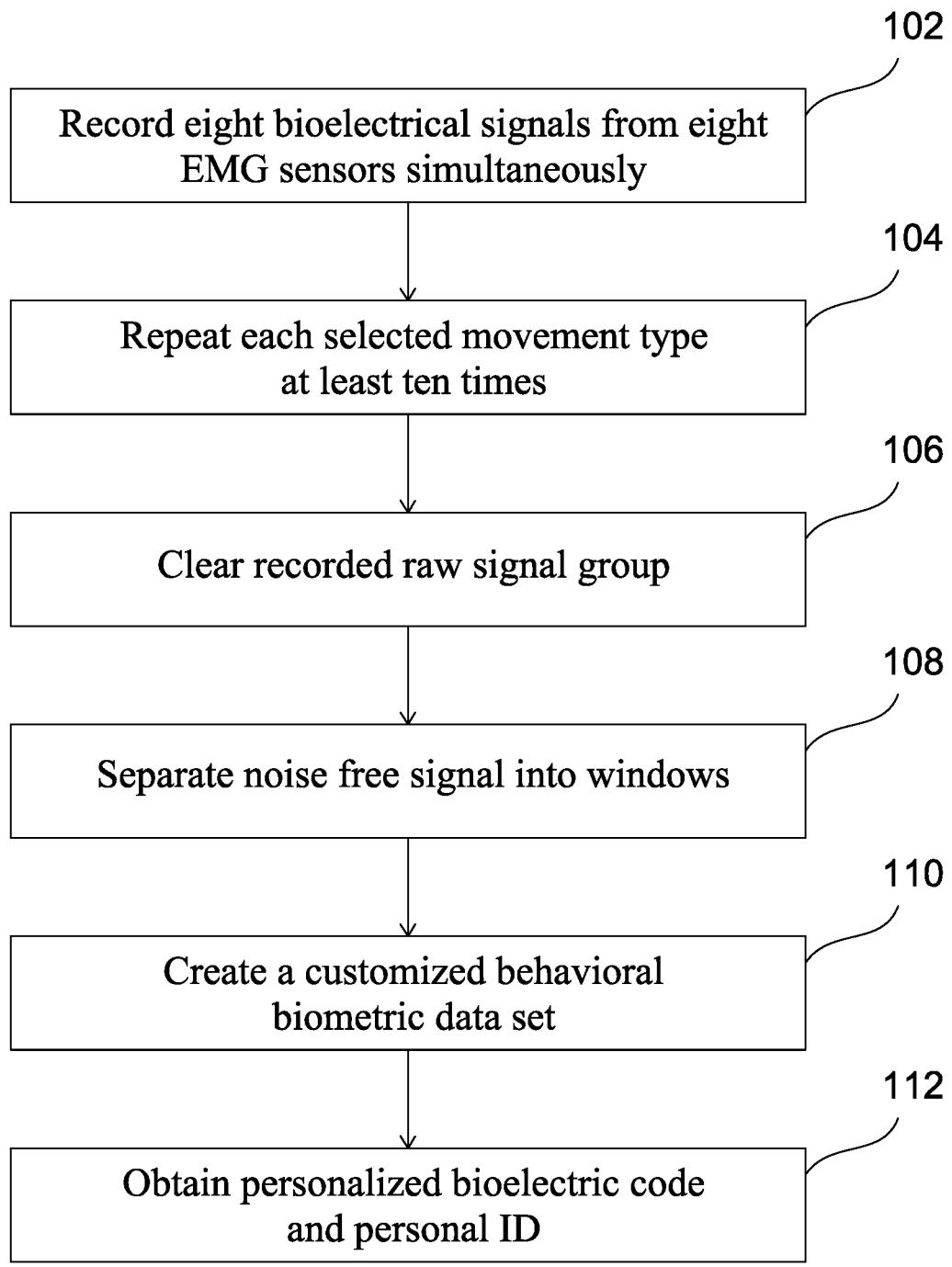

METHOD OF CREATING A PERSONAL BIOELECTRIC ID (PASSWORD) WITH HAND MOVEMENTS OF PERSON AND IDENTIFICATION OF BEHAVIORAL BIOMETRIC BASED PERSON WITH EMG SIGNALS

CROSS REFERENCE TO THE RELATED APPLICATIONS

This application is the national stage entry of International Application No. PCT/TR2019/050916, filed on Nov. 1, 2019, which is based upon and claims priority to Turkish Patent Application No. 2018/16762 filed on Nov. 7, 2018, the entire contents of which are incorporated herein by reference.

TECHNICAL FIELD

Invention is an application method of place of biometric based person recognition systems. It provides the identification of personal bioelectric code and personal ID code by identifying the persons and gestures of the person with benefit of behavioral biometric data of EMG (Electromyography) signals.

BACKGROUND

Fingerprint, face recognition, eye recognition (iris, retina, etc.), hand geometry, vein recognition (palm, finger vein, etc.), gait recognition (image processing based), signature recognition (image processing-based) systems take place in the field of Biometric Based Person Recognition Systems.

The most important disadvantage of fingerprint recognition systems is the short-term deformation of fingertips by burning, cutting, surface contact and frequent loss of marks. Another problem with fingerprint recognition is that some people do not have permanent fingerprints due to skin diseases, organ deficiency and burning. Another problem with fingerprint recognition systems is the system's error in imitation fingerprint. To overcome this problem, it is necessary to use advanced thermal sensors to test the viability of the finger from which the fingerprint was obtained. Effective use alone is not possible. Extra sensor support slows down the algorithm and increases the cost.

Although hand geometry recognition is a high accuracy method, it has disadvantages in terms of cost and usage due to the large and heavy reading device. In addition, injury, loss of fingers, gout or calcification in a number of diseases that affect the performance of the system is one of the disadvantages.

In face recognition systems, pairing is difficult because the face contains many features and too many comparisons are made.

There are about 200 reference points in iris scan for comparison, and pairing is difficult because of too many comparisons. Problems encountered in systems that use iris recognition include the inability to identify people who do not see the eyes, have nystagmus disease (trembling eyes) or who do not have irises, and the fact that the eyelids or eyelashes disrupt the iris pattern while the iris picture is taken negatively affects the system. In addition, a certain amount of light is emitted during iris image acquisition, which has a disturbing effect on people in everyday life.

Retinal recognition is the recognition of the vascular layer behind the pupil of the human eye. The biggest disadvantage of this method is that the vessel structure is easily affected and deteriorated because of some diseases.

In voice recognition system, recording environment and usage environment must be isolated from noise. Furthermore, in some negative situations, such as the speech of people in different tones and accents, the difference of the sounds produced as a result of the reflection of the emotional conditions to the sound, and the discomfort, the change of the sound is another disadvantage affecting the system.

Physical biometric systems are used in combination with card access where higher security is required. Some of the registration information is kept on the card. Thus, it is not allowed to open the door without the person's card and finger, card and retina etc. together.

It can also be used with the password entry screen where security is even more important. When both the password and card and the physical biometric data (fingerprint etc.) information are correct at the same time, the door is opened to open, which increases the time to pass through the access point (through the door etc.).

Signature recognition is divided into offline and online systems. In online systems, recognition is made by writing and evaluating pen movements with motion detectors. Many electronic equipment is required for signature verification. Pressure-sensitive tablets capture the dynamic characteristics and shape of the signature. Signing time, speed, acceleration, pressure applied to the surface of the pen are important features used in defining. Disadvantages of these systems are; The system requires a large number of appropriate samples in order to learn the speed, behavioral and other characteristics of the user and that the signature is a biometric that does not remain constant throughout life and changes over time, aging, health and mood. In offline signature verification system, recognition is performed as a result of the analysis of the wet signature. Offline signature recognition system requires less equipment than online signature recognition systems. This field examines the feature of the signature as a pattern. Another disadvantage of the offline signature recognition system is the ability to learn and imitate the pattern features of the wet signature. Another disadvantage is that some people change their signatures frequently patternually or they use habit of using different signature models such as business life and social life in different areas.

Handwriting and signature recognition systems are not as widely used as others, and its generally preferred in document security systems.

In case of contamination of biological material from which DNA will be obtained, it reduces sample quality, making it difficult to analyze. Another disadvantage of this biometry is the fact that DNA analysis is carried out over a period of 24 hours and is costly. It is not possible to apply such Fingerprints, retina, etc. systems to daily life.

The main disadvantage of writing rhythm systems is that it uses only one parameter (range and duration of key presses) for decision making. This reduces the success.

It is still sought to solve problems such as insecure storage of physical biometric data (face, iris, retina) directly in the database and occupying a lot of space.

If the biometric data is stolen, it is not possible to use that biometric data again.

Behavioral biometric data (signature, keypad rhythm) has low performance and reliability rates due to the low number of attributes used.

It is known that face and iris recognition systems which are already known as the most reliable solution do not work well in today's technology.

Another disadvantage for all biometric systems is that the recognition times are long and sometimes the interrogation is repeated several times after. That people have to wait at least 2-3 minutes at the entrance of the access control.

SUMMARY

Invention is about to identification of a personalized bioelectric code, in other words, a personal ID code, by utilizing behavioral biometric data of EMG (Electromyography) signals as an application method of field of biometric based person recognition systems. Bioelectrical signals transmitted from the brain to the lower arm muscle groups in order to provide hand movements (hand closing, hand opening, wrist inward, up and down movements, thumb-point finger contact, thumb-middle finger contact, thumb-ring finger contact, thumb-little finger contact, object pointing gesture, etc.) are recorded with biobility during movement and a personalized personal behavioral ID (code) is defined.

BRIEF DESCRIPTION OF THE DRAWING

The FIGURE is a diagram of a method of identification of a behavioral biometric based on a person by Electromyography (EMG) signals.

DETAILED DESCRIPTION OF THE EMBODIMENTS

Nerve and muscle cells in the human body are cells that can be stimulated. Electrochemical situations occurring in nerve and muscle cells produce bioelectrical potentials. Bio-electrical signals resulting from muscle contraction are called EMG (Electromyography) signals. EMG signals are analog signals. EMG signal is neither periodic nor deterministic. EMG signals are not repeated at specified time intervals and a single mathematical expression cannot represent EMG signals obtained during a recording period. EMG signals are not fixed signals. Therefore, it is not possible to artificially generate and copy the specific frequency behavior of the motor units and the resulting EMG signals.

The EMG signal is directly related to the physiology of each individual and it is individual. It has behavioural biometric data.

EMG signals depend on factors such as;

Muscle shape and size of the person, muscle fiber pattern (knitting), muscle strength-producing capacity, muscle heat distribution, Neural activity, motor unit discharge type, Age, sex, muscle development, bone density, skin fat layer and conductivity, gesture style.

The characteristics of the EMG signals are different from each other even if the appearance of the movement gestures of the two people looks the same. In other words, it has a behavioral biometric feature.

EMG signals are behavioral biometric data by taking advantage of the ability to distinguish person and person's hand movements with personalized bioelectric code that is to identify the personal ID (password) code.

As a working principle of invention, wireless EMG sensor with eight surface electrodes in wrist-shaped sensor to be attached to the arm of person records the bio-electrical signals from the lower arm muscles during movement. Each of the eight EMG sensors in the wristband records information of a muscle group in the lower arm. The signal sampling frequency of the eight EMG sensors in the wristband is 200 Hz. Sampling is defined as the instantaneous reading of the analog signal voltage at certain time intervals (depending on frequency) and storing these values as a series of numbers.

While the person performs the hand gesture (hand closing, hand opening, inward, outward and downward movements of the wrist, thumb-point finger contact, thumb-middle finger contact, thumb-ring finger contact, thumb-pinky finger contact, object pointing gesture, that is, all movements that a physical hand can do etc.) of his/her choice and wants to use it as a password, eight bioelectric signals from eight EMG sensors are recorded simultaneously in recordings (windows) of up to 10 seconds. In order to increase accuracy, each type of movement selected by the person performs at least ten repetitions. bioelectric signal group received in each repetition is recorded separately.

During recording of the bioelectric signals, various noise signals (ambient noise, magnetic effects, vibration and effect of electronic recorder) are interfered with raw EMG signals due to environmental and hardware resources. Therefore, the recorded raw signal group is purified from the noise signals by the bandpass filter.

The bioelectric signal contains some specific information (reaction speed, filling and discharging mode and duration of the motor unit constituting neural activity, maximum amplitude, energy, oscillation amount and frequency of bioelectric signal, etc.) about the person and the type of movement. This self-knowledge is directly related to the physiology of each individual and varies from person to person. In order to obtain this information (attribute), attribute extraction methods are applied to the signal.

Windowing is applied to the signal before calculating the attributes of the EMG signals. Two different methods can be used for framing. In the overlap windowing method, each new window of the segmented signal of length "R" is intersected in steps of length "r". In the adjacent method, each piece intersects with each other by the neighboring and starting points as "r". R=256 msn, r=32 msn which are generally accepted as optimum framing values for real time applications were applied for this study.

Mathematical expressions of the calculated attributes of the signals:

Signal Energy: Mathematically the energy of m (t) signal $$E = \int_{t_i}^{t_j} |m(t)| dt \qquad (1)$$

It is calculated by equation which mentioned above. Here, tj and ti show the upper and lower time limits of the part of the signal to be integrated. In the above expression, T=ti−tj refers to the area below the absolute value of the signal curve in the time interval.

Maximum Value of Signal: Maximum value of the signal represents the largest of the sampled signal values in each packet divided into windows.

Signal Variance: The variance value of the signal refers to the amount of deviation from the sampled signal values in each packet divided by windows. m(t) is the variance of the signal to express the probability density function of t;

$$VAR = \left(\frac{1}{T}\int_0^T (t - ORT)^2 m(t) dt\right) \qquad (2)$$

The attributes extracted for each transaction are individual behavioral biometric data which form a data set. Thus, personalized bioelectric code, in other words, personal ID code is obtained.

In this study, especially selected and calculated time domain attributes; energy of the signali maximum value, apart from the variance of the time domain features of the effective value of the signal, average value, zero crossing number, the length of the signal and so on. attributes, frequency domain attributes of the signal; Mean frequency, median frequency, mean peak frequency, spectral moments, frequency ratio, power spectrum ratio and variance of central frequency, etc. and can be used to create a personal ID. Personal password is defined by using the attributes mentioned. The important thing is to identify the active features and shorten the computational time by using the least number of attributes and to keep the discrimination optimal.

For any authentication system (finance, home security, door password, car lock system, etc.), the person may define the bioelectrical signal attributes corresponding to the desired hand movement (one or several movements may be in the form of group movement) through this data set as the bioelectric ID (code). Moreover, it can set a different bioelectric code for each system. The person has the chance to create as much code (personal ID) as combinations of the number of defined and classified actions.

The bioelectrical movement code defined for the person, in other words, according to the ID, identification (discernment) of the person and thus the physical places (home, car, workplace, laboratory etc.) protected by personal account (ATM, PC user account, etc.) accesses are provided by the Comparison/Person recognition algorithm.

As person recognition algorithm decision tree algorithm, nearest neighbor algorithm, artificial neural network algorithm, fuzzy logic classification algorithm and artificial fuzzy logic classification algorithms were used separately and successful results were obtained. The success of the person recognition algorithms is increased by the fact that the first recording data set, used as training data by repeating multiple times (at least ten times) for each movement.

Bioelectric signal encoded system is a biometric data that has much higher security than existing bioelectrical based person identification systems. Since the EMG signal exhibits a stochastic (random) structure, it is not possible to reproduce the signal completely or generate it with an artificial (electronic) source for each different hand pattern. Since each bioelectric signal (more than multi-channel EMG) recorded for a hand pattern is calculated and categorized according to a plurality of attributes, the individual's success in distinguishing is also very high. Different signal is transmitted from the brain to the muscles for each different movement of the person (hand close, open, thumb-toe contact etc.). This means that there is a separate set of attributes for each transaction. This allows the person to define and use an unlimited number of bioelectric codes. Even if it is never possible to steal and copy with today's technology, If the person's ID is stolen with the advances in technology, the person can set another personal ID, password and use it safely. Like other biometrics, it is no longer possible to use this data again. It is not possible to store entie an individual biometric signal in its entirely. It is enough to introduce and store the ID and the bioelectric wrist ID of the person. Like other biometric systems, security procedures such as storing the actual data by encryption and protecting it with a highly complex algorithm are not necessary. Moreover, there is no need for high storage areas because of the data set is relatively small.

After integration of this behavioral biometric data recognition system in areas such as controlled access system, electronic lock, smart home system, office, factory R & D centers etc., financial sector (ATM account access control system), users will have the following advantages:

Safety using and identifying different personal ID for each location (home, Office, bank atm, car etc.) where people are accessed with passwords, biometric data and other equipment (magnetic card, password etc.), Bio-wristband, easy to carry like wrist watch, Disappearing risks like forgetting code, stealing, Even if the EMG wristband is stolen, it is not possible to use (even if the player knows and imitates your movement pattern, it will never produce the same signal.), Eliminating the difficulty of remembering numerical password with movement password, Natural and easy to use, Time saving during controlled door entrance (such as using keys, keying in numeric keys and reading biometric data such as fingerprint iris, etc.), the signal will be transmitted and controlled by the wireless communication data before the door arrives and the door is ordered to open when pairing occurs.

Providing high security with a single access control system,

Eliminating victimhood In the financial sector (ATM, etc.) password and card theft, etc.

Individualized bioelectrical ID identification process from behavioral biometric data consists of three main steps.
1) Registration
2) Comparison
3) Verification and Access Permission In the registration (enrollment) phase; First, person goes to the place that he/she wants to identify as the movement code with biowristband and recorder then gesture code is repeated at least ten times and sample biometric registration is taken. Each recording received contains eight bioelectrical signals. By applying preprocessing and feature extraction methods to this signal group, the movement code, ID, data set of the person is created.

During the comparison and verification phase; each time the person passes through the device, identification of the person is made by comparing the data taken with the calculated attribute set, the attribute set (personal transaction password, id) calculated from the first record data. The success of the comparison algorithm can be increased when first record, in other words the training data set increase. This means; training the algorithm of the invention, that is, in order to better teach the person's signals to the invention, the person records as much movement variation as possible during the first recording.

In the access permit phase; If the data is stored in the system each time the person passes the system is authorized to access the system (home, car, laboratory door, etc.)— account access (ATM account, PC account, etc.) is allowed, or access is restricted.

With reference to the FIGURE, [B] a method 100 of behavioral biometric based person recognition with EMG signals and the creation of a personalized bioelectrical id (code) by person's hand movements include steps below;

Person who wishing to create a password wear the wristband,

At step 102, eight bioelectric signals from eight EMG sensors are recorded simultaneously in hand movements of up to 10 sec recordings (windows), At step 104, each selected movement type is repeated by the person at least ten times, At step 106, clearing the recorded raw signal group from noise signals with bandpass filter, At step 108, separation of noise free signal into windows (R=256, r=32 ms), At step 110, creating a customized behavioral biometric data set with the extracted attributes for each transaction, At step 112, obtaining personalized bioelectric code and personal ID (code).

What is claimed is:

1. A method of identification of a behavioral biometric based on a person by Electromyography (EMG) signals and creation of a personalized bioelectrical code and a personal ID code by hand movements of the person, comprising the steps of:

simultaneously sensing, by eight EMG sensors, bioelectrical signals transmitted from a brain of the person to lower arm muscle groups of the person to provide the hand movements, wherein the bioelectrical signals are recorded in eight bioelectric signals from the eight EMG sensors in a wristband worn by the person with windows of up to 10 seconds, wherein the eight EMG sensors in the wristband have a signal sampling frequency of 200 Hz, repeating sensing and recording bioelectrical signals for each type of the hand movements selected by the person for at least ten times, clearing, from the recorded bioelectrical signals, a recorded raw signal group from noise signals with a bandpass filter, separating a signal cleared from the noise signals within time windows, wherein each time window of length R is intersected in steps of length r, with R=256 ms and r=32 ms, creating a customized behavioral biometric data set with generated attributes for each transaction, and obtaining the personalized bioelectrical code and the personal ID code in response to the creating the customized behavioral biometric data set, wherein said personalized bioelectrical code and the personal ID code are obtained using the customized behavioral biometric data set.

* * * * *